US00PP32863P2

(12) United States Plant Patent
O'Connell

(10) Patent No.: US PP32,863 P2
(45) Date of Patent: Mar. 2, 2021

(54) ***ALOE* PLANT NAMED 'NIGHT SKY'**

(50) Latin Name: ***Aloe* hybrid**
Varietal Denomination: NIGHT SKY

(71) Applicant: Altman Specialty Plants, Inc, Vista, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 16/873,313

(22) Filed: Mar. 17, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

PUBLICATIONS

Ebay website for 'Starry Night'. https://www.ebay.com/itm/283028020658ebay website for 'Starry Night'. Downloaded Jul. 27, 2020. 6 pages. (Year: 2018).*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Aloe* plant named 'NIGHT SKY' is disclosed, characterized by star shaped rosettes of olive green, with some dappling of white spots, and blushes an attractive bronze in full sun. Plants of the new variety root easily, grow larger than many colorful commercial miniature *Aloes*, and offset prolifically, quickly filling an 8 inch or larger container and growing larger. Due to the prolific offsetting propagation rates are enhanced. The new variety is an *Aloe*, typically produced as a garden or container plant.

2 Drawing Sheets

Figure 1:
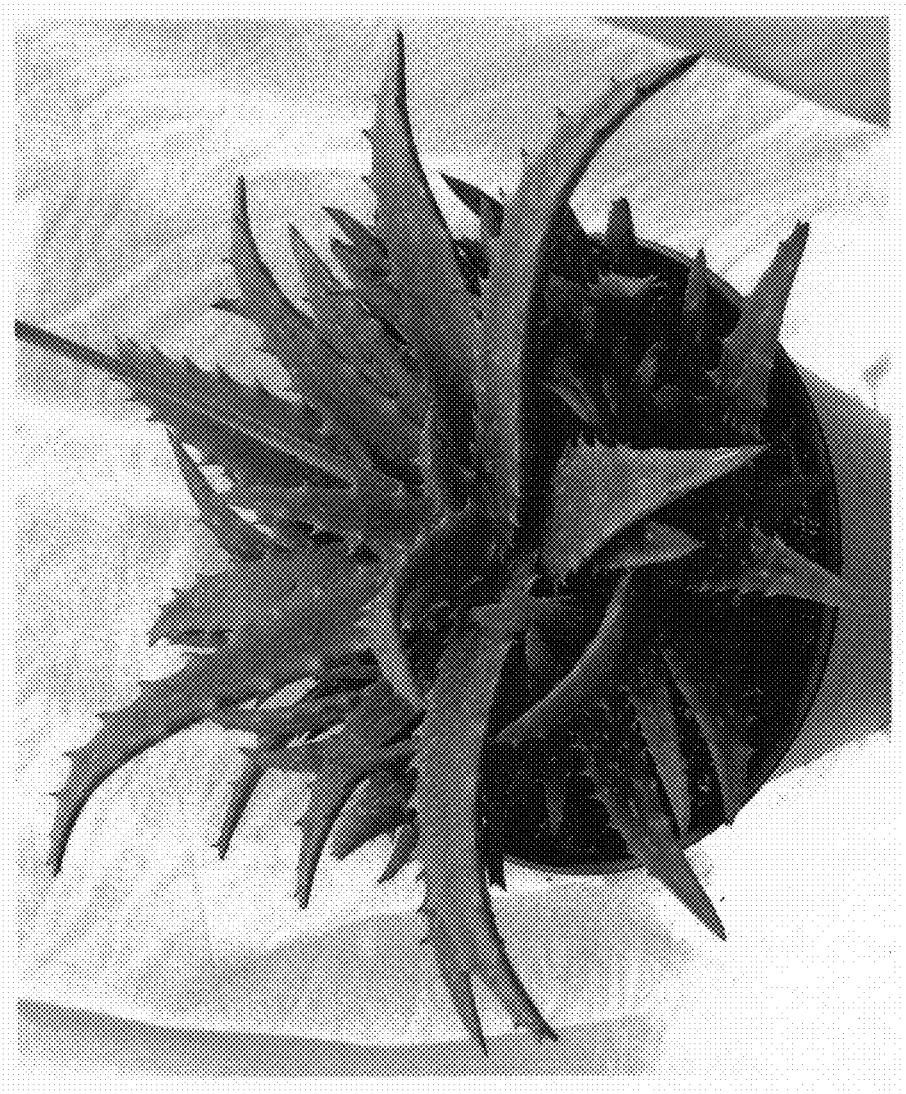

Latin name of the genus and species: *Aloe* hybrid.
Variety denomination: 'NIGHT SKY'.

BACKGROUND OF THE INVENTION

The new cultivar is a product of a planned breeding program. The seed parent is the unpatented *Aloe* hybrid 'CO11'. The pollen parent is the unpatented *Aloe* hybrid 'SRH 3'. The crossing was made in March 2015 at a commercial greenhouse in Vista, Calif. 'NIGHT SKY' was selected by the inventor in July 2016.

Asexual reproduction of the new cultivar 'NIGHT SKY' was first performed by vegetative cuttings at a commercial laboratory in Vista, Calif. in Summer of 2017. 'NIGHT SKY' has since produced several generations and has shown that the unique features of this cultivar are stable and reproduced true to type.

SUMMARY OF THE INVENTION

The cultivar 'NIGHT SKY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NIGHT SKY'. These characteristics in combination distinguish 'NIGHT SKY' as a new and distinct *Aloe* cultivar:

1. *Aloe* 'Starry Night' prolifically produces offsets, quickly filling an 8" or larger container.

2. *Aloe* 'Starry Night' grows larger than many of the popular new colorful miniature *Aloes* that have been introduced into the commercial market.
3. *Aloe* 'NIGHT SKY' has a moderately fast growth rate, and is quick to root, sometimes within days, whereas many other *Aloes* are slow growers and do not root for weeks.
4. *Aloe* 'NIGHT SKY', due to the prolific production of offsets, enhances propagation rates in a commercial nursery.
5. *Aloe* 'NIGHT SKY' forms star shaped rosettes of olive green, with some dappling of white spots, and blushes an attractive bronze in full sun.

PARENTAL COMPARISON

Plants of the new cultivar 'NIGHT SKY' are similar to the seed parent in most horticultural characteristics. However, plants of the new variety differ from the seed parent in the following:

1. *Aloe* NIGHT SKY' displays larger rosettes than does *Aloe* 'CO11'.
2. *Aloe* 'NIGHT SKY' produces more offsets than does *Aloe* 'CO11'.
3. *Aloe* 'NIGHT SKY' is of a lower and flatter morphology than is *Aloe* 'CO11'.
4. *Aloe* 'NIGHT SKY' exhibits a taller, fuller inflorescence than does *Aloe* 'CO11'.
5. *Aloe* 'NIGHT SKY' displays dappled white spots on the olive green leaves whereas *Aloe* 'CO11' does not.

Plants of the new cultivar 'NIGHT SKY' are similar to the pollen parent in most horticultural characteristics. However, plants of the new variety differ in the following:

1. *Aloe* 'NIGHT SKY' produces more serrate margins than does *Aloe* 'SRH 3'.
2. *Aloe* 'NIGHT SKY' has a faster growth rate than does *Aloe* 'SRH 3'.
3. *Aloe* 'NIGHT SKY' displays an attractive bronzing color of the leaves in full sun whereas *Aloe* 'SRH 3' does not.
4. *Aloe* 'NIGHT SKY' produces a slightly less full inflorescence than does *Aloe* 'SRH 3'.

COMMERCIAL COMPARISON

'NIGHT SKY' can be compared to the unpatented commercial variety *Aloe distans*. The two *Aloe* varieties are similar in most horticultural characteristics; however, the new variety differs in the following:

1. *Aloe* 'NIGHT SKY' forms attractive compact clusters whereas *Aloe distans* displays stems of taller, but somewhat recumbent stature and does not typically offset until a larger specimen.
2. *Aloe* 'NIGHT SKY' offsets profusely, whereas *Aloe distans* is slower to produce offsets and produces fewer offsets.
3. *Aloe* 'NIGHT SKY', due to its prolific offsettting, quick rooting of the offsets, and lack of losses during the propagation process, enhances propagation rates in a commercial nursery whereas *Aloe distans* is slower to propagate and suffers losses to rot during the propagation process.

'NIGHT SKY' can be compared to the unpatented commercial variety *Aloe barbadensis* (*Aloe vera*). The two *Aloe* varieties are similar in most horticultural characteristics; however, the new variety differs in the following:

1. *Aloe* 'NIGHT SKY' forms attractive, low growing clusters of green, star-shaped rosettes dappled with white spots, whereas *Aloe barbadensis* (*Aloe vera*) produces glaucous grayish green, upright stems with few offsets.
2. *Aloe* 'NIGHT SKY' displays an attractive, slightly capitate inflorescence of larger orange flowers whereas *Aloe barbadensis* (*Aloe vera*) produces a yellow inflorescence.
3. *Aloe* 'NIGHT SKY', due to its prolific offsetting, enhances propagation in a commercial environment, whereas *Aloe barbadensis* (*Aloe vera*) produces few offsets.

BRIEF DESCRIPTION OF THE PHOTOGRAPHS

The accompanying photograph in FIG. 1 illustrates in full color a typical plant of 'NIGHT SKY' grown in a greenhouse in Vista, Calif. This plant is approximately 10 months old, shown in a 1 gallon container.

Figure 2:
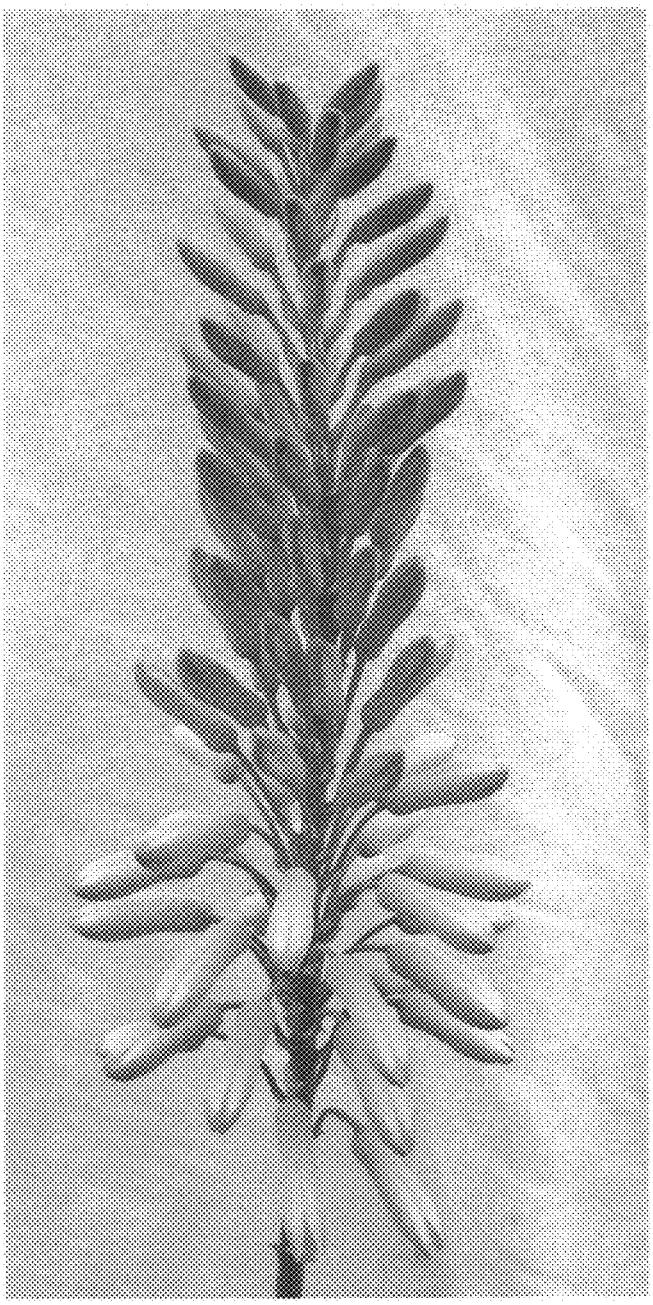

FIG. 2 illustrates a close up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'NIGHT SKY' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'NIGHT SKY'.

Age of the plant described: About 1 year.

PROPAGATION

Time to initiate roots: Approximately 25 days at 22° C.

Root description: Fibrous. Brown, not accurately measured with The R.H.S. chart.

Propagation method: Vegetative divisions or tissue culture.

PLANT

Growth habit: Upright rosette, offsetting to form clumps with time.

Container size: 2 gallon.

Height: Approximately 14 cm to top of highest leaf. Approximately 50 cm to top of highest inflorescence.

Plant spread: Approximately 35 cm.

Growth rate: Moderate.

Branching characteristics: Offsets from base of plant.

Quantity of offsets: 12 to 15.

FOLIAGE

Leaf:

*Arrangement*.—Rosette.

*Average length*.—Average range 10-20 cm.

*Average width*.—5 cm.

*Average thickness*.—About 5 mm.

*Shape of blade*.—Lanceolate, slightly deltoid.

*Apex*.—Acute.

*Base*.—Clasping.

*Margin*.—Sharp dentations occurring at regular intervals of 1.5 to 2 cm.

*Texture of top surface*.—Smooth.

*Texture of bottom surface*.—Smooth.

*Quantity of leaves*.—Approximately 12 to 15 per mature rosette.

*Color*.—Young foliage upper side: Near RHS Yellow-Green 147A flushed Greyed-Red 178B. Young foliage under side: Near RHS Green 137C. Mature foliage upper side: Near RHS Green 137A. Dentations near Greyed-Red 178B. Sparse to moderate dappling of spots colored near RHS White 155A. Mature foliage under side: Near RHS Green 137A. Dentations near Greyed-Red 178B. Sparse dappling of spots colored near RHS White 155A.

*Venation*.—Linear. Color: Indistinguishable from leaf blade.

FLOWER

Natural flowering season: Late Fall to early Winter in Southern California.

Inflorescence type and habit: Raceme.

Flower longevity on plant: About 1.5 months.

Quantity of flowers: 40 to 50 on average.

Total inflorescence size:

*Height*.—Approximately 20 cm.

*Width*.—Approximately 6.5 cm.

Flower bud:
*Shape*.—Cylindrical.
*Length*.—Approximately 1.5 cm.
*Diameter*.—Approximately 7 mm.
*Color*.—Near RHS Orange 28B, apex near Yellow-Green 145A.

Corolla:
*Arrangement*.—Tubular, opening slightly at apex with age.
*Length*.—Approximately 3.0 to 3.5 cm.
*Width*.—Approximately 1.0 cm at widest point.
*Color*.—
*Immature*.—Outer Surface: Near RHS Orange 28B, apex near Yellow-Green 145B lightly streaked Yellow 2B. Inner Surface: RHS Orange 26B, apex near Yellow-Green 145B lightly streaked Yellow 2D.
*Mature*.—Outer Surface: Near RHS Orange 28C, upper ⅓ Yellow-Orange 18C. Apex flushed Yellow-Green 145B. Inner Surface: RHS Orange 26C, apex near Yellow-Green 145c lightly streaked Yellow 2D.

Calyx: Absent.

Fragrance: None.

Pedicel:
*Length*.—Approximately 2.5 cm.
*Width*.—2-3 mm.
*Aspect*.—Upright when immature, dropping slightly at maturity.
*Color*.—Near RHS Orange 28A when immature, near Orange-Red 30D at maturity.

Peduncle:
*Length*.—Approximately 30 cm.
*Width*.—7 mm.
*Aspect*.—Upright when immature, dropping slightly at maturity.
*Color*.—Near RHS Yellow-Green 147C.

REPRODUCTIVE ORGANS

Stamens:
*Number*.—6.
*Filament length*.—2.5 cm.
*Filament color*.—RHS Yellow 4D.
*Anther length*.—About 3 mm.
*Anther color*.—RHS Yellow 13A.
*Anther shape*.—Oval.
*Pollen color*.—RHS Yellow-Orange 14B.

Pistil:
*Number*.—1.
*Length*.—Approximately 2.5 cm.
*Style color*.—RHS Yellow 4D.
*Stigma*.—Shape: Linear. Color: RHS Yellow 4D. Ovary color: RHS Green 143C.

OTHER CHARACTERISTICS

Seeds and fruits: Not observed to date.

Temperature tolerance: Tolerates temperatures from approximately 28° C. to 0° C.

Disease/pest resistance: Neither resistance no susceptibility observed.

What is claimed is:

1. A new and distinct cultivar of *Aloe* plant named 'NIGHT SKY' as herein illustrated and described.

* * * * *